US00PP12509P2

(12) United States Plant Patent
Taylor

(10) Patent No.: US PP12,509 P2
(45) Date of Patent: Apr. 2, 2002

(54) NECTARINE PLANT NAMED 'TAYLOR 14L22'

(75) Inventor: James W. Taylor, Dinuba, CA (US)

(73) Assignee: Ito Packing Co., Reedley, CA (US)

( * ) Notice: Subject to any disclaimer, the term of this patent is extended or adjusted under 35 U.S.C. 154(b) by 0 days.

(21) Appl. No.: 09/468,255

(22) Filed: Dec. 20, 1999

(51) Int. Cl.[7] ..... A01H 5/00

(52) U.S. Cl. ..... Plt./190

(58) Field of Search ..... Plt./190

*Primary Examiner*—Bruce R. Campell
*Assistant Examiner*—Susan B. McCormick
(74) *Attorney, Agent, or Firm*—Dennis B. Haase

(57) ABSTRACT

A new and distinct variety of nectarine tree with fruit of yellow fleshed cling stone type, maturing in the early part of the season and exhibiting good eating quality, bearing fruit of deeper red color, firmer flesh and larger size than other varieties of the same season.

1 Drawing Sheet

BACKGROUND OF THE VARIETY

The present invention relates to a new and distinct variety of nectarine tree, which I refer to as Taylor 14L22, of a yellow fleshed, cling stone fruit, attractive in appearance, maturing in the early season period, which was developed from a continued fruit breeding program.

ORIGIN AND ASEXUAL REPRODUCTION OF THE NEW VARIETY

This invention was derived from an ongoing fruit breeding to improve nectarines in regard to consumer quality and market acceptability.

The development was the result of flowers of the big Jim variety (U.S. Plant Pat. No. 8,021) being emasculated and pollinated with pollen from an early maturing variety obtained from earlier hybridizing work known as 4K14A. Seeds produced by this method were stratified and grown to a height of about 18 inches. These seedlings were then bud grafted into dehorned orchard trees in the experimental orchard of Ito Packing Co., Reedley, Calif., and tested under the variety number of 14L22.

SUMMARY OF THE VARIETY

The instant variety, developed through the above described method, was selected because of its excellent eating quality. The novel nectarine of the present invention has a much more attractive deep red color and larger size than other varieties ripening at the same period.

BRIEF DESCRIPTION OF THE DRAWINGS

The accompnaying drawing illustrates typical specimens of the fruit and foliage of my new variety as grown in the San Joaquin Valley of Calif. Two specimens are shown, one of which is in side elevation and the other from the apex view. Yet another specimen is sectioned, and a side elevation is depicted, illustrating the internal texture and color of the flesh and pit. A sprig of the plant is also illustrated, emphasizing the structure and appearance of the leaves.

DETAILED DESCRIPTION

The following is a detailed description of my new variety with color reference being from the *Maerz and Paul Dictionary of Colors*, (reference Form PTO/SB/20) except in the instance where terminology having generally understood meaning is employed.

Parentage: Big Jim (U.S. Plant Pat. No. 8,021)×unnamed selection F1.

Propagation: Maintains its distinguishing characteristics through several bud graft generations.

Locality where grown and observed: Near Reedley, County of Fresno, Calif.

Tree

Size: Large; vigorous; spreading; open; vase form; productive; regular bearer.

Trunk: Medium size; average diameter of 8 to 12 inches depending on the root stalk and the growing conditions; medium texture; color of dark brown to grey depending on the sloughing of the cortex.

Branches: Spreading; size is 8 to 10 feet depending on the pruning and roping of the limbs; wider growth habit than most varieties of nectarines.

Lenticels: Similar to those on the young shoots on other nectarine and peach varieties.

Vigor: Vigorous, productive.

Regularity of bearing: Regular bearer.

Leaves:

*Color*.—Top side — 32B9; under side 31I8.

*Size*.—Average length, 5 inches; average width, 1.2 inches, medium thickness.

*Margin*.—Glandular; crenate.

*Petiole*.—Medium length; medium thickness.

*Glands*.—Average number — four; opposite; medium size; reniform; position, usually two at the base of the leaf blade near the attachment of the petiole and occasionally one on the petiole near the leaf blade.

Flower bud: Medium size.

Flowers: Large; showy.

Petals: Normally five, but may tend to double with 8 to 10 petals, or occasionally more petals.

Color: Pink (2E3).

Date of full bloom: Five to ten days earlier than the variety Red Jim (U.S. Plant Pat. No. 4,518).

Anthers: Red.

Pollen: Similar to other nectarine varieties except for gene sequence which was not run.

FRUIT

Maturity:

*When described.*—First ripe, May 26, 1994.

Date of first picking: May 28, 1994.

Date of last picking: Jun. 8, 1994.

Size:

*Average axial length.*—2.52 inches; average transverse width in the suture plane 2.64.

Form: Essentially round.

Suture: Ventral suture is shallow but deepens toward the apex and extends slightly beyond the apex and extends toward the dorsal side. The dorsal suture is very shallow.

Ventral surface: Smooth.

*Stem.*—Short, about the same depth as the cavity.

*Stem cavity.*—Round, medium depth (average depth ⅜ inches).

*Base.*—Flattened slightly.

*Apex.*—Recessed in the suture.

*Skin.*—Medium thick; medium texture.

*Tendency to crack.*—None observed.

*Bloom.*—No bloom.

*Color.*—Base color in early stages of ripening the color is a deep red (6I11), then darkens as the fruit matures to a very dark red (5K12).

Flesh:

*Texture.*—Very firm in the early states of maturity, then continues to be firm through the ripening stage so that it can be picked at full maturity without bruising, thus allowing for the full growth size before harvesting.

*Color.*—Yellow (9K6), flecked with red color in early stages of maturity, especially around the fruit fibers (2H11). The red color increases and darkens as the fruit matures (6K11).

*Juice.*—Abundant.

*Flavor.*—Good balance of acid and sugar.

*Aroma.*—Typical of yellow fleshed nectarines.

*Fibers.*—Running through.

*Ripening.*—Evenly.

*Eating quality.*—Excellent with good balance between sugar and acid.

Stone:

*Adherence to the flesh.*—Cling stone.

*Size.*—Average thickness ¾ inch; average width 1 1/16 inch; average length 1¼ inches.

*Form.*—Oval.

*Apex.*—Usually short but can occasionally have a longer point.

*Hilum.*—Small, oblong.

*Dorsal edge.*—Shallow grooves.

*Ventral edge.*—Narrow, shallow.

*Surface.*—Irregularly pitted; shallow with occasional deeper groove toward the apex.

*Color.*—Light reddish brown (3D8).

Use: Fresh market.

Keeping quality: Excellent.

Resistance to disease: Similar to other glanded varieties of nectarine varieties.

Athough this novel variety of nectarine possesses the described characteristics as a result of the growing conditions in the Reedley area of Fresno County, Calif., in the central portion of the San Joaquin Valley, it is to be understood that variations of the usual magnitude in characteristic incident to the growing conditions, fertilization, pruning and pest control are to be expected.

Having thus described and illustrated my new nectarine tree, what is new and desired to be secured by Letters Patent is:

1. A new and distinct nectarine tree as herein described and illustrated, with fruit of yellow fleshed cling stone type, having a maturity period in the early part of the season with good eating quality, bearing fruit of deeper red color, firmer flesh and larger size than other varieties at this season.

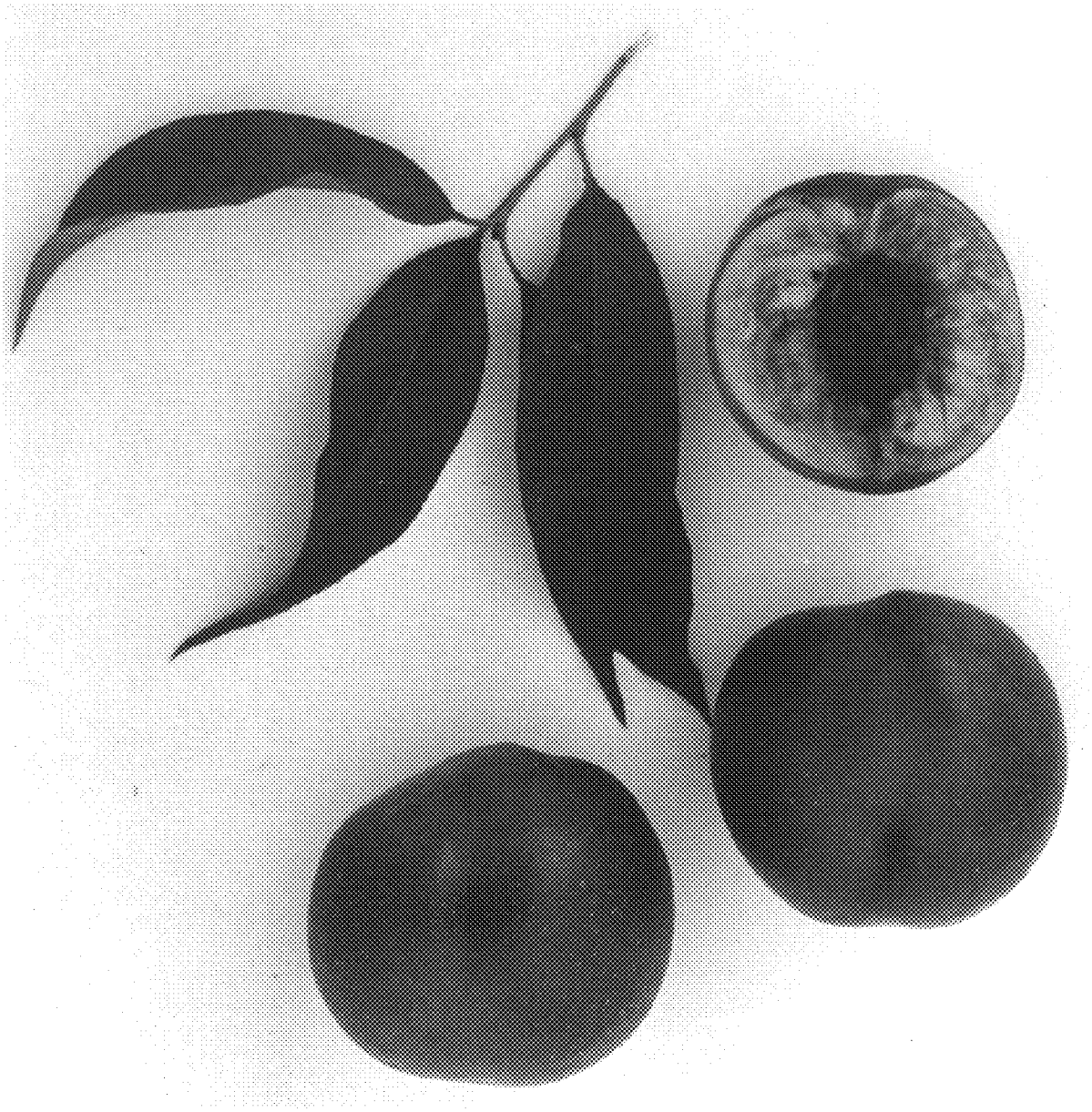

* * * * *